United States Patent [19]

Soika

[11] Patent Number: 4,574,456
[45] Date of Patent: Mar. 11, 1986

[54] METHOD OF MANUFACTURING A SUPPORT ASSEMBLY
[75] Inventor: Emil H. Soika, Mundelein, Ill.
[73] Assignee: Baxter Travenol Laboratories, Inc., Deerfield, Ill.
[21] Appl. No.: 517,547
[22] Filed: Sep. 7, 1983

Related U.S. Application Data

[62] Division of Ser. No. 326,739, Dec. 2, 1981, Pat. No. 4,413,992.
[51] Int. Cl.$^4$ ............................................. B23P 11/02
[52] U.S. Cl. ...................................... 29/451; 29/469; 29/525
[58] Field of Search ................. 29/450, 451, 525, 469; 604/51, 93, 111, 263, 264, 272, 280, 283, 403, 411, 412, 408

[56] References Cited

U.S. PATENT DOCUMENTS

| Re. 28,713 | 2/1976 | Stevens et al. . |
|---|---|---|
| 777,065 | 12/1904 | Boardman . |
| 1,057,860 | 4/1913 | Lind . |
| 1,100,799 | 6/1914 | Wedig . |
| 1,476,103 | 12/1923 | Platt et al. . |
| 1,529,659 | 3/1925 | Marcy . |
| 2,689,562 | 9/1954 | Adams et al. . |
| 2,702,037 | 2/1955 | Walter . |
| 2,705,008 | 3/1955 | Melton . |
| 2,712,822 | 7/1955 | Gewecke ............................ 604/263 |
| 2,716,982 | 9/1955 | Ryan . |
| 2,794,435 | 6/1957 | Stevens . |
| 2,847,994 | 8/1958 | Huber . |
| 2,847,995 | 8/1958 | Adams . |
| 2,902,995 | 9/1959 | Loper . |
| 2,949,913 | 8/1960 | Gewecke et al. . |
| 3,043,304 | 7/1962 | Higgins . |
| 3,073,307 | 1/1963 | Stevens . |
| 3,096,763 | 7/1963 | McConnaughey et al. . |
| 3,127,892 | 4/1964 | Bellamy, Jr. et al. . |
| 3,196,672 | 7/1965 | Katz . |
| 3,217,710 | 11/1965 | Beall et al. . |
| 3,227,121 | 1/1966 | Speetjens et al. . |
| 3,330,278 | 7/1967 | Santomieri . |
| 3,342,179 | 9/1967 | Ellmann ............................ 604/408 |
| 3,367,331 | 2/1968 | Brookfield . |
| 3,367,488 | 2/1983 | Hamilton . |
| 3,406,687 | 10/1968 | Moyer . |
| 3,434,473 | 3/1969 | Smith . |
| 3,523,530 | 8/1970 | Pagones .............................. 604/263 |
| 3,638,650 | 2/1972 | Burke et al. . |
| 3,640,275 | 2/1972 | Burke et al. . |
| 3,662,457 | 5/1972 | Gores . |
| 3,677,247 | 7/1972 | Brown . |
| 3,820,652 | 6/1974 | Thackston . |
| 3,889,673 | 6/1975 | Dovey et al. . |
| 4,078,565 | 3/1978 | Genese . |
| 4,091,811 | 5/1978 | Bates et al. ......................... 604/263 |
| 4,121,588 | 10/1978 | Geiger . |
| 4,178,930 | 12/1979 | Fisher, Jr. . |
| 4,180,071 | 12/1979 | Oiwa . |
| 4,192,305 | 3/1980 | Seberg . |
| 4,193,399 | 3/1980 | Robinson . |
| 4,227,527 | 10/1980 | DeFrank et al. .................... 604/263 |
| 4,240,427 | 12/1980 | Akhavi . |
| 4,266,543 | 5/1981 | Blum . |
| 4,326,518 | 4/1982 | Williams . |
| 4,391,029 | 7/1983 | Czuba et al. ........................ 29/450 |

FOREIGN PATENT DOCUMENTS

| 159814 | 11/1954 | Australia . |
|---|---|---|
| 545415 | 8/1957 | Canada . |
| 934405 | 9/1973 | Canada ............................... 604/283 |
| 1085652 | 2/1959 | Fed. Rep. of Germany . |
| 498057 | 9/1954 | Italy . |
| 810860 | 3/1959 | United Kingdom . |
| 840487 | 7/1960 | United Kingdom . |

Primary Examiner—Charlie T. Moon
Attorney, Agent, or Firm—Paul C. Flattery; Daniel D. Ryan; Bradford R. L. Price

[57] ABSTRACT

A cannula support assembly comprises a hub subassembly, which supports the cannula, and a cover subassembly, which attaches to the hub subassembly to sealingly enclose the cannula prior to use and which can be easily removed from and subsequently reattached to the hub subassembly, if desired. Each subassembly is itself preferably fabricated from one or more individually extruded component parts which can be assembled together in a manner lending itself to cost efficient, automated production techniques and which thereby obviates the use of substantially more costly injection molded or compression molded plastic parts. The resulting support assembly is durable, easily attachable to flexible tubing, and readily adaptable to diverse uses, such as a hub and cover for a phlebotomy needle or an inline sampling needle.

12 Claims, 11 Drawing Figures

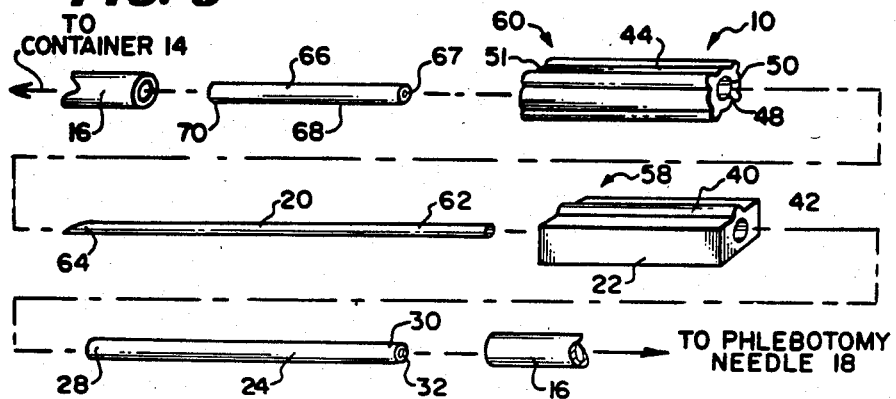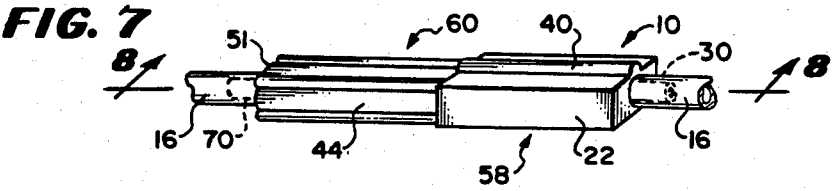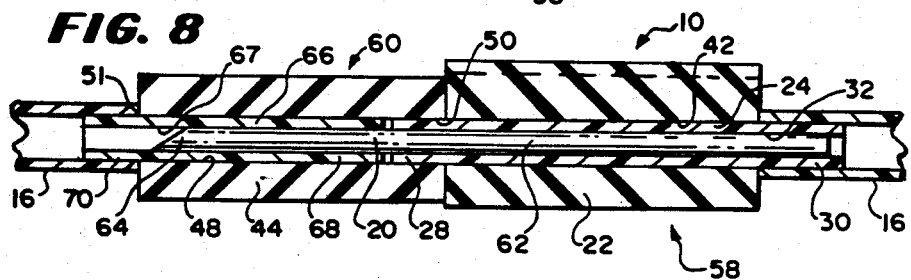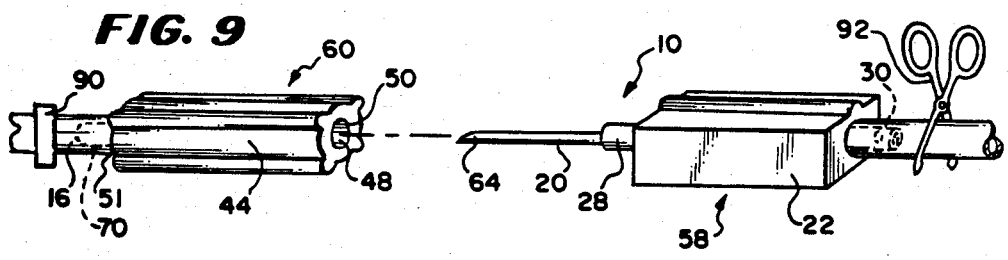

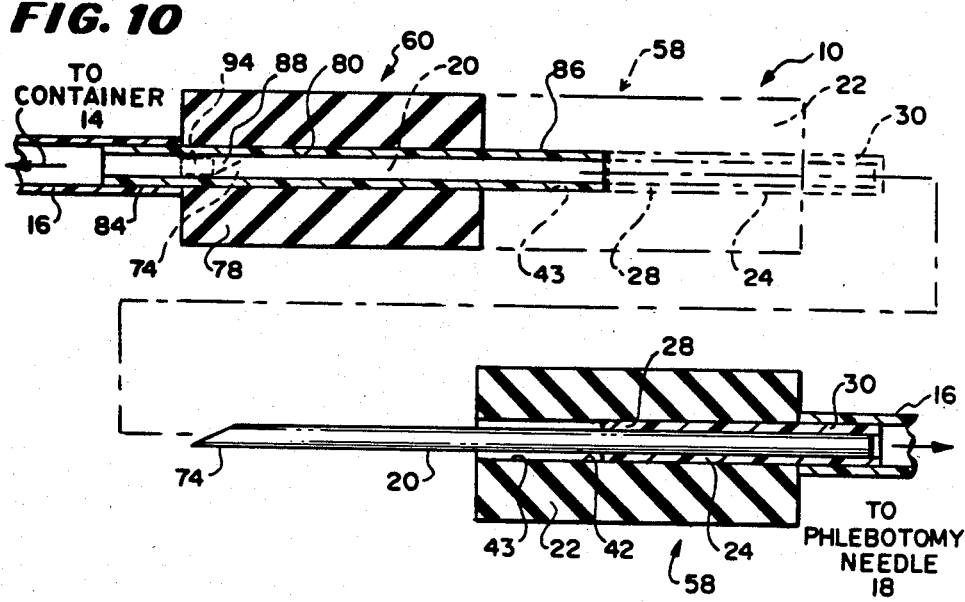

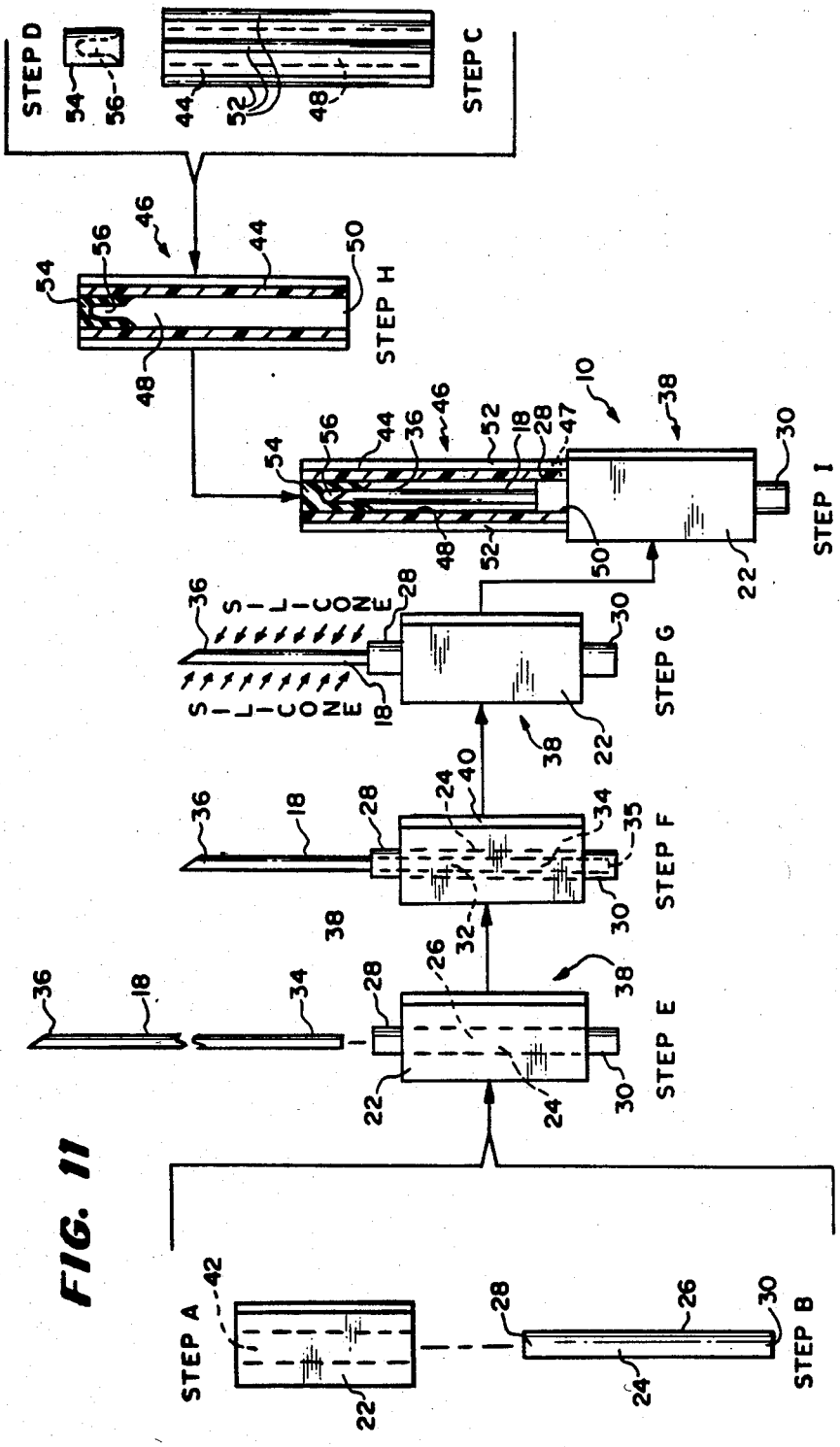

METHOD OF MANUFACTURING A SUPPORT ASSEMBLY

This is a division of application Ser. No. 326,739, filed Dec. 2, 1981, now U.S. Pat. No. 4,413,992.

TECHNICAL FIELD OF THE INVENTION

The invention generally relates to cannula support assemblies and to methods for manufacturing such assemblies. The invention more particularly relates to cannula support assemblies which accommodate attachment to flexible tubing.

DESCRIPTION OF THE PRIOR ART

Cannulas in the form of catheters, hypodermic needles, phlebotomy needles, and the like are widely used to administer and draw blood and other parenteral fluids These cannulas are typically carried in specially designed support members, or hubs, such as those discussed in the following U.S. patents:

| Gewecke | 2,712,822 | July 12, 1955 |
| McConnaughey et al | 3,096,763 | July 9, 1963 |
| Santomieri | 3,330,278 | July 11, 1967 |
| Moyer | 3,406,687 | October 22, 1968 |
| Stevens et al Re. | 28,713 | February 17, 1976 |
| Seberg | 4,192,305 | March 11, 1980 |
| Akhavi | 4,240,427 | December 23, 1980 |
| Blum | 4,266,543 | May 12, 1981 |

Cannula support members are also the subject of the following foreign documents:

| British Patent Specification | 810,860 |
| British Patent Specification | 840,487 |
| Canadian Patent | 545,415 |
| German Patent | 664,001 |
| German Auslegeschrift | 1,085,652 |
| Italian Patent | 498,057 |

Cover members, or sheaths, are often provided to protect the sterile integrity of the cannulas prior to use. Cannula support assemblies having cover members or sheaths are discussed in the following U.S. patents:

| Wedig | 1,100,799 | June 23, 1914 |
| Walter | 2,702,037 | February 15, 1955 |
| Melton | 2,705,008 | March 29, 1955 |
| Brookfield | 3,294,089 | December 27, 1966 |
| Pagones | 3,523,530 | August 11, 1970 |
| Geiger | 4,121,588 | October 24, 1978 |
| Oiwa | 4,180,071 | December 25, 1979 |

A cover member or sheath for a cannula is also discussed in Australian Pat. No. 159,814.

Some cannula support assemblies are particularly designed for attachment to a hypodermic syringe, such as those discussed in the above-cited Marcy, McConnaughey, Santomieri, Moyer, Stevens, and Geiger patents.

Other cannula support assemblies are particularly designed to enable attachment to flexible tubing, such as those discussed in the above-cited Walter, Gewecke, and Pagones Patents.

One of the principal objects of this invention is to provide a cannula support assembly which is compact and durable and which lends itself to cost efficient production on a large scale, automated basis.

Another principal object of this invention is to provide a cannula support assembly having a cover member which encloses the cannula prior to use and which can be easily removed and returned as desired.

Yet another principal object of this invention is to provide a cannula support assembly which, in addition to the above-listed features, is easily attachable to flexible tubing.

SUMMARY OF THE INVENTION

To achieve these and other objects, the invention provides a cannula support assembly comprising several individually fabricated component parts which can be assembled together in a manner lending itself to cost efficient, large scale manufacturing techniques.

In one embodiment, the support assembly comprises a first, or outer, member and a second, or inner, member disposed within the first member. The second member has a bore which accommodates the shank of the cannula and supports the operative end of the cannula in an outwardly exposed position beyond one side of the first member. An end of the second member extends outwardly beyond the opposite side of the first member for facile attachment to a fluid conduit. Together, the first and second members form a hub subassembly for the cannula.

In a preferred embodiment, the first and second members of the hub subassembly take the form of tubular bodies each having an essentially uniform cross-sectional shape and being mutually fashioned so that the second tubular member can be accommodated in a secure manner within the bore of the first tubular member.

This construction permits the manufacture of the first and second members by known ram or screw extrusion techniques, and thereby obviates the need for substantially more costly injection molded plastic or compression molded rubber parts. This construction also readily accommodates the use of automated manufacturing processes to fabricate the hub subassembly on a large scale basis.

In one embodiment, the ends of the second member extend outwardly beyond the respective opposite sides of the first member. In this arrangement, the assembly includes a third member having an open interior which accommodates the outwardly exposed portion of the cannula. The third member includes an end which removably engages the outwardly extending end of the second member from which the cannula projects to secure the third member to the hub subassembly with the heretofore exposed portion of the cannula enclosed within the open confines of the third member. The third member thus constitutes a cover subassembly for the cannula which can be easily removed from and subsequently reattached to the cannula hub.

In one embodiment, the open interior of the cover subassembly is spaced radially outwardly of, and is thus disposed in a noncontiguous relationship with, the exterior of the entire outwardly projecting portion of the cannula. In this arrangement, the cannula support assembly includes a fourth member which is insertable into the outermost portion of the open interior of the third member. The fourth member includes a pocket which, when the cover subassembly is secured to the hub subassembly, sealingly encloses only the outermost tip of the outwardly projecting cannula. By virtue of this construction, physical contact with the outwardly projecting portion of the cannula is avoided, except at its outermost tip.

This construction all but eliminates the generation of friction and suction during the removal and return of the cover subassembly onto the hub subassembly. If a silicon coating is applied to the cannula in order to promote a more comfortable venipuncture, this construction also serves to preserve the silicon coating against friction loss.

This construction also positively seals the cannula from fluid loss and preserves the sterile integrity of the cannula while, at the same time, facilitates the removal and return of the cover subassembly when desired. For these reasons, this construction is ideally suited for use of the assembly in association with a phlebotomy needle.

In a preferred embodiment, the third member, like the first and second members, takes the form of a tubular body having an essentially uniform cross-sectional shape lending itself to manufacture by extrusion. The fourth member is a compression molded piece which can be press-fitted into the open interior of the extruded third member. This construction of the cover subassembly, coupled with the preferred construction of the hub subassembly heretofore described, accommodates the use of automated manufacturing techniques to separately fabricate the hub and cover subassemblies and to join them together to form the completed cannula support assembly.

In an alternate embodiment of the assembly, the cover subassembly comprises a tubular outer member having oppositely spaced open ends and a tubular inner member which is carried within the bore of the tubular outer member with one inner member end disposed outwardly of one end of the outer member for attachment to a fluid conduit. The other end of the inner member is confined within a portion of the outer member bore, so that the other end of the outer member remains open. In this arrangement, the outwardly exposed end of the second member which is associated with the heretofore described hub subassembly, and from which end the cannula projects, is removably engagable in a fluid-tight fit within the open end of the outer member, with the tip of the cannula extending into the confined end of the inner member and enclosed in a fluid-tight manner within the inner member bore. The fit secures this alternate embodiment of the cover subassembly to the hub subassembly of the previously described embodiment and provides for the flow of fluids through the secured-together hub and cover subassemblies.

This construction is ideally suited for use of the cannula support assembly as a hub and cover for a sampling needle which can be carried inline with a section of flexible tubing.

As in the other embodiments, both the tubular inner and outer members of the just described cover subassembly preferably have essentially uniform cross-sectional shapes which lend themselves to manufacture by extrusion and the assembly of the members, as well as their attachment to the hub subassembly, by automated techniques.

The invention also provides a method of assembling the individually extruded members of the heretofore described embodiments in a straightforward and cost efficient manner which facilitates automated production techniques and which is inherently superior to more costly and involved injection molding processes.

Other features and advantages of the embodiments of the invention will become apparent upon reviewing the following more detailed description, the drawings, and the appended claims.

DESCRIPTION OF THE DRAWINGS

FIG. 6 is an exploded perspective view of the cannula support assembly used in association with the blood sampling needle shown in FIG. 1;

FIG. 7 is an assembled perspective view of the cannula support assembly shown in FIG. 6 in a coupled relationship;

FIG. 8 is a section view of the cannula support assembly taken generally along line 8—8 in FIG. 7;

FIG. 9 is a perspective view of the cannula support assembly shown in FIG. 6 in a uncoupled relationship;

FIG. 10 is a section view of an alternate embodiment of the cannula support assembly which embodies various of the features of the invention and which is suited for use in association with either the phlebotomy needle or the sampling needle; and FIG. 11 is a diagrammatic flow chart, with parts broken away and in section, showing a method of assembling the cannula support assembly which embodies various of the features of the invention.

Figure 1:
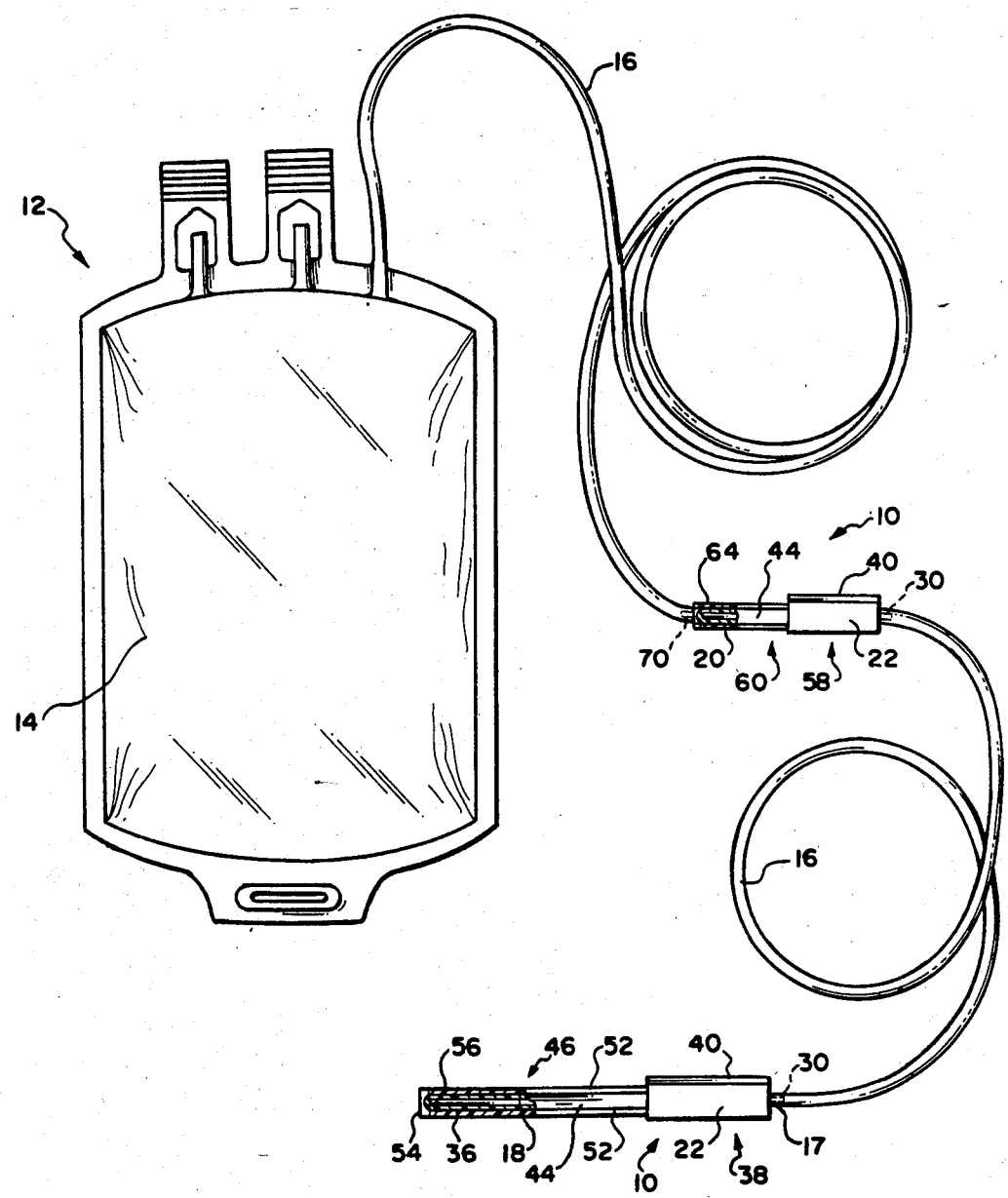
FIG. 1 is a plan view, with parts broken away and in section, of a blood collection, storage, and sampling unit, which includes a donor tube having a phlebotomy needle and an inline blood sampling needle, each of which is carried by a cannula support assembly which embodies various of the features of the invention.

Before explaining the embodiments of the invention in detail, it is to be understood that the invention is not limited in its application to the details of construction and the arrangement of components as set forth in the following description or as illustrated in the accompanying drawings. The invention is capable of other embodiments and of being practiced or carried out in various ways. Furthermore, it is to be understood that the phraseology and terminology employed herein is for the purpose of description and should not be regarded as limiting.

DESCRIPTION OF THE PREFERRED EMBODIMENTS

A cannula support assembly 10 is shown in the drawings. The term "cannula" is used herein to broadly signify a small tube which is insertable into a body cavity, duct, or vessel. Examples of cannulas include catheters, hypodermic needles, and phlebotomy needles.

The assembly 10 which will be described herein is applicable for use in a diverse number of environments and in conjunction with catheters, hypodermic needles, and various other needle arrangements used to direct and channel blood, parenteral fluids, and medicines to and from the body. The assembly 10 is particularly well suited for interconnecting a cannula body with flexible tubing. For this reason, the illustrated embodiments envision this specific use.

Reference is first made to FIG. 1, in which a blood collection, storage, and sampling unit 12 is shown. While various constructions are possible, in the illustrated embodiment, the unit 12 includes a blood collection container 14, which typically is a flexible bag made of medical grade polyvinyl chloride plastic material. A donor tube 16, which typically is also made of a flexible medical grade polyvinyl chloride plastic material, is integrally attached to and carried by the container 14. A cannula body in the form of a phlebotomy needle 18 is attached in flow communication with the outer end 17 of the donor tube 16. The needle 18 serves after venipuncture to channel blood from a patient or donor through the donor tube 16 and into the container 14.

Another cannula body in the form of a blood sampling needle 20 is attached in line with the donor tube 16 upstream of the phlebotomy needle 18. The sampling needle 20 enables an attendant to obtain blood samples for laboratory purposes and testing after completion of the blood collection procedure.

In this specific operative environment, one embodiment of the cannula support assembly 10 is utilized to support the phlebotomy needle 18 and to attach the needle 18 to the end 17 of the donor tube 16. This embodiment of the support assembly 10 is shown in FIGS. 2 through 5.

Another embodiment of the cannula support assembly 10 is utilized to support the sampling needle 20 and to attach the needle 20 inline with the donor tube 16. This embodiment of the support assembly 10 is shown in FIGS. 6 through 9.

Figure 4:
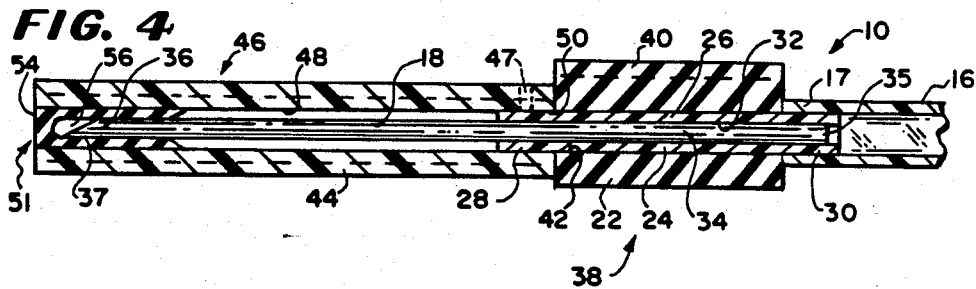
FIG. 4 is a section view of the cannula support assembly taken generally along line 4—4 in FIG. 3.

Reference is first made to FIGS. 2 through 5 and to the embodiment of the assembly 10 utilized to support the phlebotomy needle 18. In this embodiment, the assembly 10 includes a hub subassembly 38 which is compact and easily handled and manipulated between the fingertips of the attendant (see FIG. 5). The hub subassembly 38 comprises a first member 22 and a second member 24. As is best shown in FIG. 4, the second member 24 has a main body portion 26, which is carried within the first member 22, and opposite end portions, respectively 28 and 30, each of which is disposed outwardly of the first member 22.

The second member 24 has a bore 32 which extends between the two opposite end portions 28 and 30. As can be seen in FIG. 4, the bore 32 accommodates the shank 34 of the phlebotomy needle 18 with the operative, or beveled, end 36 of the needle 18 supported in an outwardly projecting, exposed position beyond one of the second member end portions, which, in the illustrated embodiment, is end portion 28 (see, in particular, FIGS. 4 and 5).

The other outwardly disposed end 30 of the second member 24 readily accommodates attachment of the hub assembly 38 to the end 17 of the donor tube 16. As is shown in FIG. 4, it is preferred that the shank end 35 of the needle 18 be disposed in closely adjacent relationship to the terminus of the second member end 30. The shank end 35 of the needle 18 thus proves interior rigidity and support for the second member end 30 to facilitate its attachment of the donor tube end 17. The shank end 35 thus also helps maintain the interior dimension of the second member 24 during exposure to heat, such as during autoclaving. The shank 34 of the needle 18 can be secured within the second member bore 32 by adhesive or epoxy bonding.

The first member 22 preferably includes an outwardly projecting ridge or shoulder 40 which extends along one exterior surface axially of the second member bore 32. This ridge 40 serves as a reference point for the proper alignment of the beveled end 36 of the needle 18 relative to the hub subassembly 38 during the assembly process. Proper bevel orientation is desirable, because it assures that the sharpest part of the needle 18 breaks the skin during venipuncture.

In addition to facilitating the initial alignment of the beveled end 36 of the needle 18 during the assembly process, the ridge 40 functions as a visual and tactile guide in the hands of the attendant (see FIG. 5) to assist him or her in positioning the beveled end 36 during venipuncture.

Figure 2:
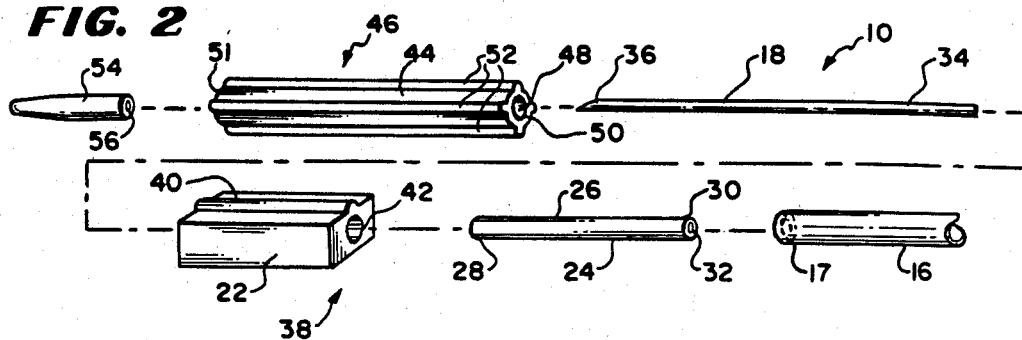
FIG. 2 is an exploded perspective view of the cannula support assembly used in association with the phlebotomy needle shown in FIG. 1.
Figure 3:
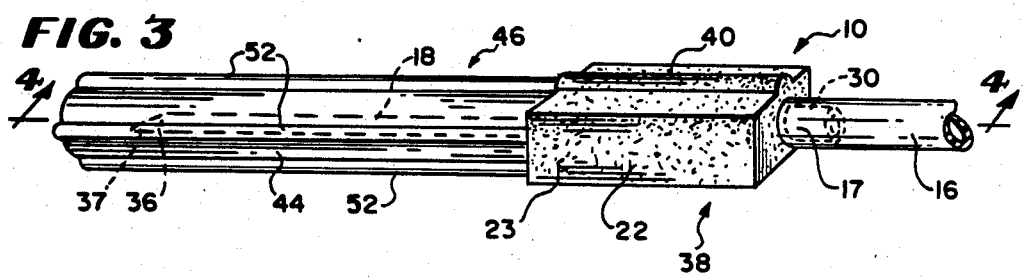
FIG. 3 is an assembled perspective view of the cannula support assembly shown in FIG. 2.

The first and second members 22 and 24 of the hub subassembly 38 may be variously constructed. However, in the illustrated and preferred embodiment (as best shown in FIG. 2), the first and second members 22 and 24 each take an elongated, tubular form having an essentially uniform cross-sectional shape. This construction enables the manufacture of the first and second members 22 and 24 utilizing known ram or screw extrusion techniques.

In this arrangement, the first and second members 22 and 24 are each preferably made of an extrudable plastic material, such as polyvinyl chloride, which is capable of withstanding autoclaving with no loss of function or evidence of distortion and which is readily bondable, such as by solvent bonding or by friction fit with heat bonding, to the polyvinyl chloride plastic of the donor tubing 16.

Figure 5:
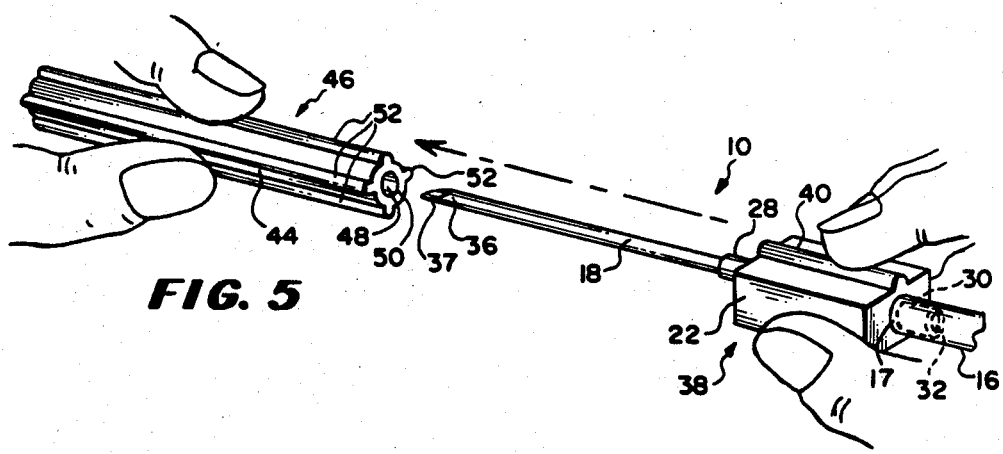
FIG. 5 is a perspective view of the cannula support assembly shown in FIG. 2 being held by an attendant with the cover member removed to expose the cannula.

The first member 22 is preferably semi-rigid or flexible in construction. This enables the attendant to effect a firm finger grip on the hub subassembly 38 (as shown in FIG. 5) and to carefully maneuver and control the hub subassembly 38 for a fast and comfortable venipuncture. The first member 22 can also be provided with a roughened exterior surface 23 (see FIG. 3), to further enhance the attendant's grip on and control of the hub subassembly 38.

In this arrangement, the main body portion 26 of the extruded second member 24 is preferably carried in an interference, or friction, fit relationship within the bore 42 which is formed during the extrusion of the tubular first member 22 (see FIGS. 2 and 4). To facilitate this desired interference fit, as well as provide for the rigid support of the needle 18, the second member 24 is preferably rigid in construction.

In an alternate arrangement, the rigid second member 24 could be inserted in a slip-fit fashion within the first member bore 42 and secured therein by use of an adhesive or solvent bond.

To protect the sterile integrity of the phlebotomy needle 18 prior to venipuncture, and to selectively seal the needle 18 against fluid loss prior to and after use, the assembly 10 includes a cover subassembly 46 which is removably attachable and reattachable to the hub subassembly 38.

The cover assembly 46 can be variously constructed. In the embodiment illustrated in FIGS. 2 through 4, the cover subassembly 46 includes a third member 44 which has an open interior 48 to accommodate the exposed portion 36 of the needle 18. The third member 44 also has an open end 50 which is removably engagable in an interference, and hence fluid-tight, fit about the outwardly disposed second member end portion 28 from which the phlebotomy needle 18 extends (see FIG. 4).

This interference, or telescopic, fit securely joins the cover subassembly 46 to the hub subassembly 38 (as shown in FIG. 4), with the outwardly disposed portion 36 of the needle 18 enclosed within the open interior 48. To further enhance the junction, a breakable thermal tack or spot weld 47 (shown in phantom lines in FIG. 4) between the end 50 and end portion 28 could be utilized.

While the third member 44 of the cover subassembly 46 may take various forms, the third member 44 preferably takes an elongated, tubular form (see FIG. 2) having an essentially uniform cross-sectional shape with oppositely spaced open ends 50 and 51, between which the open interior 48 (constituting the bore of the tubular third member 44) extends. As with the preferred construction of the first and second members 22 and 24, this elongated, tubular, and generally uniform configuration enables the manufacture of the third member 44 utilizing known ram or screw extrusion processes. Axially extending and uniformly radially spaced ridges 52 may be formed on the exterior of the third member 44 during extrusion to facilitate manipulation of the third member 44 by the attendant.

It is desirable that the extruded third member 44 be made of a rigid or semi-rigid material which, like the heretofore described first and second members 22 and 24, is capable of withstanding autoclaving with no loss of function or evidence of distortion.

As can be seen in FIG. 4, the interior diameter of the open interior 48 of the third member 44 preferably exceeds the exterior diameter of the exposed portion 36 of the phlebotomy needle 18. Thus, when the cover subassembly 46 is disposed on the hub subassembly 38, the open interior 48 is spaced radially outwardly of, and is thus disposed in a non-contiguous relationship with, the needle 18 along its entire outwardly disposed length.

In order to affect a fluid-tight seal about the needle 18 within the open interior 48 of the third member 44, the cover subassembly 46 shown in the FIGS. 2 through 5 embodiment includes a fourth member 54 which is preferably formed of a resiliently compressible material, such as compression molded rubber. The fourth member 54 is insertable in a press-fit relationship through the outermost disposed open end 51 of the third member 44 to occupy the outermost portion of the open interior 48 (see FIG. 4).

As can be seen in FIG. 4, the fourth member 54 includes a chamber or pocket 56 which is configured to sealingly envelop the outermost tip 37 of the beveled end 36 of the needle 18 when the hub and cover subassemblied 38 and 46 are joined together. The pocket 56 thereby seals the needle tip 37 from communication with the remainder of the open interior 48 of the third member 44 and provides a positive fluid shut-off for the needle 18 within the open interior 48. The heretofore described telescopic fit between the third member end 50 and the second member end 28 provides the fluid-tight seal between the open interior 48 and the atmosphere to complete the hermetic seal between the hub and cover subassemblies 38 and 46.

Leakage of fluid from the needle 18 is thus prevented when the cover subassembly 46 is attached to the hub subassembly 38. By the same mechanism, the sterile integrity of the outwardly projecting portion 36 of the needle 18 can be preserved prior to use.

Also by virtue of this construction, the cover subassembly 46 can be removed from the hub subassembly 38 when it is desired to expose the needle 18 for use (see FIG. 5). By the same token, the cover subassembly 46 can be thereafter reattached to the hub subassembly 38 when it is desired to again shield the needle 18. The open end 50 and the open interior of the third member 44, both of which are fashioned to avoid contact with the exposed portion of the needle 18, accommodate this removal and re-entry of the needle 18 into and out of the cover subassembly 46.

In addition, and as can be best seen in FIG. 4, by virtue of the heretofore described construction of the cover subassembly 46, only the outermost tip 37 of the needle 18 is in sealing contact with the pocket 56 of the fourth member 54. Thus, during removal of the cover subassembly 46 to expose the needle 18, there is a minimum of friction, or drag, created between the needle 18 and the cover subassembly 46. Such removal thus does not tend to draw or suck fluid out of the needle 18. By the same token, return of the cover subassembly 46 onto the hub subassembly 38 is achieved with a minimum of effort.

Recognizing also that it is desirable to silicon coat the exterior of the phlebotomy needle 18 to facilitate a more comfortable venipuncture, the very limited physical contact between the needle 18 and the cover subassembly 46 shown in FIGS. 2 through 5 further serves to protect the silicon coating along most of the outwardly exposed portion 36 of the needle 18 against friction loss during removal or return of the cover subassembly 46. This construction thus also ultimately contributes to a more comfortable venipuncture.

In addition to the above-described benefits the construction of the hub and cover subassemblies 38 and 46, the same construction readily lends itself to mass production, automated manufacturing techniques, such as on a continuous assembly line or an indexing turntable. The flow of such a construction process is shown in FIG. 11.

In this process, the first, second, and third members 22, 24, and 44 are each separately formed by extrusion in continuous elongated pieces which are then cut to the desired size. This is generally shown by the steps designated A, B, and C in FIG. 11.

The dimensions of the first, second, and third members 22, 24, and 44 can vary according to the size of the needle 18 utilized, the interior diameter of the donor tube 12, and the perceived preferences of the attendant. In one operative embodiment, in which a 15 or 16 gauge phlebotomy needle 18 is utilized, the first member 22 is approximately 0.8 inch long with an interior bore diameter of approximately 0.12 inch; the second member 24 is approximately 1.2 inches long with an outside diameter of approximately 0.13 inch (thereby forming the preferred interference fit within the first member bore) and an interior bore diameter of approximately 0.07 inch; and the third member 44 is approximately 1.7 inches long with an outside diameter of approximately 0.22 inch and a, interior bore diameter (i.e. the diameter of the open interior 48 and the end 50) of approximately 0.12 inch (thereby forming the preferred interference fit with the exposed second member end 28).

As is generally shown in the step designated D in FIG. 11, the fourth member 54 is individually compression molded. The dimensions of the fourth member 54 are selected to generally correspond with the dimensions of the third member 44, so that a snug press-fit between the two can be affected. In the context of the above-described operative embodiment of the third member 44, the fourth member 54 is approximately 0.7 inch long, with an outside diameter of approximately 0.13 inch and an inside diameter of the pocket 56 of approximately 0.06 inch. It should be noted that the outer peripheral edges of the pocket 56 are outwardly beveled to facilitate the insertion of the needle tip 37 into the sealing fit within the interior region of the pocket 56 (see also FIG. 4).

As is generally shown in the step designated E in FIG. 11, during the manufacturing process, the second member 24 is inserted in its interference fit within the bore 42 of the first member 22 to form the hub subassembly 38. As is next shown in the step designated F, the shank 34 of the needle 18 is thereafter inserted into the second member bore 32, with the shank end 35 being preferably disposed approximately 1/16th of an inch from the end 30. The beveled end portion 36 of the needle 18 is properly aligned relative to the orientation ridge 40 during step F, and the shank 34 is secured by an adhesive or epoxy bond within the second member bore 32. It has been observed that proper bevel orientation of within plus or minus 10 degrees can be achieved utilizing this method.

Preferably, and as is generally shown in the step designated G in FIG. 11, the outwardly exposed portion 36 of the needle 10 is then siliconized.

Meanwhile, and as is generally shown in the step designated H in FIG. 11, the fourth member 54 is press-fitted within the member 44 to form the cover subassembly 46. As is next shown in the step designated I in FIG. 11, the cover subassembly 46 is thereafter fitted on the exposed second member end 28 of the hub subassembly 38. If desired, the tack weld 47 (shown in phantom lines) can be formed by suitable means.

The assembly 10 can thereafter be sterilized by autoclaving. The assemely 10 can be attached to flexible tubing prior to or after sterilization.

Reference is now made principally to FIGS. 6 through 9 and to the embodiment of the cannula support assembly 10 associated with the sampling needle 20.

This embodiment is similar in many respects to the support assembly embodiment associated with the phlebotomy needle 18. For this reason, common structural elements are assigned common reference numerals.

The assembly 10 shown in FIGS. 6 through 9 includes a sampling needle support, or hub, subassembly 58 and a needle insert, or cover, subassembly 60.

The needle support subassembly 58, like the hub subassembly 38 of the first described embodiment, includes first and second members, respectively 22 and 24, each having a bore, respectively 42 and 32. Also like the first described hub subassembly 38, the second member 24 is preferably disposed in an interference fit within the first member bore 42, with its end portions 28 and 30 each projecting outwardly from the first member 22.

The second member bore 32 of the second embodiment accommodates the shank 62 of the sampling needle 20, just as the shank 34 of the phlebotomy needle 18 of the first embodiment is accommodated in its associated second member bore 32. The beveled end 64 of the sampling needle 20 is thereby supported in the same outwardly projecting exposed position beyond the second member end 28, and is properly aligned relative to the orientation shoulder 40.

The needle insert subassembly 60 of the FIGS. 6 through 9 embodiment, like the cover subassembly 46 of the first embodiment, includes a third member 44 having an open interior 48 to accommodate the exposed portion 64 of the sampling needle 20. Also like the first described cover assembly 46, the third member 44 of the needle insert assembly 60 has an open end 50 which is removably engagable in an interference, fluid-tight fit about the outwardly disposed second member end portion 28 from which the sampling needle 20 extends (see FIG. 8). This fit securely couples the hub and cover subassemblies 58 and 60 together.

However, unlike the first described cover assembly 46, which utilizes the fourth member 54 to plug the opposite end 51 of the third member 44 and seal the needle tip 37, the cover assembly 60 includes a tubular member 66 having a bore 67 which accommodates the beveled end 64 of the sampling needle 20 is an essentially fluid-tight fit. The tubular member 66 has one end 68 which is disposed in an interference fit within a portion of the open interior 48 to receive the beveled needle end 64. An opposite end 70 of the tubular member 66 extends outwardly from the end 51 of the third member 44 for facile attachment to the donor tube 16 downstream of the container 14. Another portion of the donor tube 16 is likewise attached to the outwardly extending end 30 of the second member 24 upstream of the phlebotomy needle 18 (see FIG. 1).

When coupled together, as is shown in FIGS. 7 and 8, the needle support and insert portions 58 and 60 15 afford the flow of fluid through the sampling needle 20 between the phlebotomy needle 18 and the container 14. The fluid-tight fit of the beveled end 64 of the needle 20 within the bore 67, coupled with the fluid-tight connection between the subassemblies 58 and 60 provided by the engagement of the open end 50 about the second member end 28, prevents the leakage of fluid outwardly of the assembly 10.

However, the needle insert subassembly 60 may be easily separated from the needle support subassembly 60, if desired (see FIG. 9), to interrupt the fluid flow between the phlebotomy needle 18 and the container 14 and to afford the drawing of fluid samples through the needle 20. In the context of the illustrated use, the subassemblies 58 and 60 are typically separated after a unit of blood has been collected in the container 14. Prior to separation, the donor tube 16 should be first permanently sealed upstream of the insert subassembly 68, such as by use of a hand sealer clip 90. The donor tube 16 should also be temporarily clamped at this time, such as be use of a hemostat 92, downstream of the support subassembly 58.

Separation of the subassemblies 58 and 60 can proceed, as shown in FIG. 9. By selectively releasing the hemostat 92, one or more blood samples of the collected blood may be obtained through the blood sampling needle 20 for laboratory tests and the like utilizing the pre-existing phlebotomy.

As in the construction of the support assembly 10 associated with the phlebotomy needle 18, the first and second members 22 and 24 of the sampling needle support subassembly 58 and the members 44 and 66 of the sampling needle insert subassembly 60 each preferably take an elongated, tubular form (see FIG. 6) having an essentially uniform cross-sectional shape enabling manufacture by a ram or screw extrusion process.

Likewise, the second member 24 of the support and subassembly 58 is the tubular member 66 of the insert assembly 60 are preferably rigid in construction. The other associated members 22 and 44 may each be rigid or semi-rigid in construction.

The various extruded component parts of the sampling needle support subassembly 58 and the sampling needle insert subassembly 60 can be individually extruded and cut and then assembled together, utilizing a process substantially identical to that heretofore described and shown in FIG. 7. In the process associated with the second embodiment, however, the tubular member 66 would be extruded in Step D and then inserted during Step H into its interference fit within the open interior 48 through the end 51 to form the sampling needle insert subassembly 60 shown in FIGS. 6 through 9.

As with the assembly 10 associated with the phlebotomy needle 18, the dimensions of the component parts associated with the hub subassembly 58 and cover subassembly 60 of the second embodiment can vary according to the size of the sampling needle 20 utilized, the interior diameter of the donor tube 16, and the perceived preferences of the attendant.

It should be appreciated that the particular construction enabling a fluid-tight connection between the subassemblies 22 and 24 in the first embodiment and 58 and 60 in the second embodiment can vary. An alternate arrangement of the sampling needle support assembly 10 is shown in FIG. 10, with structural elements common to those heretofore discussed assigned common reference numerals.

In this arrangement, the second member 24 of the needle support assembly 58 occupies only a portion of the associated first member bore 42, with one end 30 (as in the previous embodiments) disposed outwardly for attachment with the donor tubing 16 upstream or the phlebotomy needle 18, and the other end 28, from which the needle 20 extends, confined or recessed within the bore 42, leaving a portion 43 of the bore 42 oven or unoccupied by the second member 24.

In this arrangement, the insert subassembly 60 includes a first, or outer, member 78 and a second, or inner, member 80 carried by the outer member 78. The inner member 80 includes opposite end portions 84 and 86, each of which is disposed outwardly the outer member 78, and a bore 88 which extends between the two opposite end portions 84 and 86. One end 84 of the inner member 80 accommodates attachment to the donor tube 16 downstream of the blood collection container 14. As is shown in phantom lines in FIG. 10, the other end 86 is open to accommodate passage the outwardly exposed beveled end 74 of the sampling needle 20 into a snug fluid-tight fit within the inner member bore 88. As is also shown in phantom lines in FIG. 10, at the same time the end 86 is removably engagable in an interference, fluid-tight fit within the unoccupied portion 43 of the first member bore 42, thereby coupling the two subassemblies 58 and 60.

Should use of the alternate arrangement shown in FIG. 10 be desired in association with a phlebotomy needle, the end 84 of the inner member 80 would be terminated generally coextensively, or flush, against the adjacent terminal side of the outer member 76 and suitably sealed with a plug member 94 (shown in phantom lines in FIG. 10). The subassembly 60, so modified, would serve generally the same purposes of the heretofore described cover subassembly 46 of the first embodiment.

In any of the embodiment of the cannula support assembly 10 herein discussed, sterilization by autoclaving has been envisioned. However, the assembly 10 does lend itself to gas sterilization techniques, such as by use of ethylene oxide. For example, to adopt the phlebotomy needle support assembly 10 of the FIGS. 2 through 5 and FIG. 10 embodiments to gas sterilization, the fourth member 54 of the first embodiment and the plug 94 of the FIG. 10 embodiment can take the form of a microporous plug, such as one made from sintered microporous polyethylene available under the trademark POREX from Glassrock Products, Inc., of Atlanta, Ga. and as disclosed in De Frank et al, U.S. Pat. No. 4,227,527. The plug 94 prevents the passage of microorganisms but allows the influx of sterilizing gas into the cover subassembly 46 or 60 (phantom line variation in FIG. 10).

It is important to appreciate the fact that the utilization of members of tubular, essentially uniform cross-sectional shape enables the use of extruded pieces and a straightforward assembly line or turntable-type mass production method as shown in FIG. 11. The invention thus substantially obviates the need for injection molded plastic or compression mold parts which are in widespread use today. This significantly simplifies construction methods and significantly reduces attendant expenses for materials and labor.

Furthermore, the cannula support assembly 10 of any of the embodiments show is compact, durable, and able to withstand rough handling during bulk packaging and shipment, as well as during use.

In addition, the cannula support assembly 10 of any of the embodiments is readily adaptable to different needle sizes (gauge and length), component shapes, and material. For example, should a larger size needle be required, the length of the components associated with the associated hub and cover subassemblies need only to be increased. Should a different gauge needle be required, the interior dimensions of the associated subassemblies need only to be correspondingly changed to accommodate the different gauge.

It should be apparent to those skilled in the art that the assembly 10 and its associated method of manufacture are readily adaptable to uses other than those particularly shown and discussed herein. Indeed, the numerous specific embodiments which have been heretofore discussed and which all share common component parts only underscore the significant versatility and adaptability of the assembly 10 which embodies the features of the invention.

Various of the features of the invention are set forth in the following claims.

I claim:

1. A method of manufacturing a support assembly for cannula having an operative end, said method comprising steps of fabricating a first member having a bore and a uniform cross-sectional shape, fabricating a second member having a generally uniform cross-sectional shape with opposite ends and a bore extending therebetween which accommodates the cannula, inserting the second member into the bore of the first member with at least one end of the second member extending outwardly of the first member, securing the cannula with the bore of the second member so that the operative end of the cannula is supported in an outwardly exposed position beyond the end of the second member opposite to the first mentioned second member end, and subsequent to said fabrication, insertion and steps, joining a fluid conduit to the first mentioned second end.

2. A method according to claim 1 wherin said second member insertion step includes inserting the second member into the bore of the first member with both opposite ends of the second member extending outwardly of the first member.

3. A method according to claim 2 and further including the steps of
fabricating a third member having a generally uniform cross-sectional shape with an open interior and an open end to form a cover for the cannula, and
joining the cannula cover to the cannula hub with the open end of the cannula cover engaged in a fluid-tight relationship about the outwardly disposed end of the second member from which the cannula extends with the operative end of the cannula enclosed within the open interior of the cannula cover.

4. A method according to claim 3 wherein said fabrication steps of the first, second, and third members includes extruding each of the members.

5. A method according to claim 3 and further including the steps of
fabricating a resiliently compressible fourth member, and
press-fitting the fourth member into the open interior of the cannula cover to sealingly enclose both the end of the cannula cover and the tip of the operative cannula end which is disposed therein when the cover is engaged on the hub.

6. A method according to claim 3 and further including the steps of
fabricating a tubular member having a generally uniform cross-sectional shape, and
mounting the tubular member upon the member with an end portion of the tubular member extending into the open interior thereof to sealingly enclose the operative cannula end which is disposed therein when the cover is engaged on the hub and an opposite end extending outwardly of the third member for attachment to a fluid conduit.

7. A method according to claim 1 wherein said second member insertion step includes inserting the second member into the bore of the first member with the end from which the cannula extends confined within the bore of the first member.

8. A method according to claim 7 and further including the steps of
fabricating an outer member having a bore and a generally uniform cross-sectional shape,
fabricating an inner member having a generally uniform cross-sectional shape with opposite ends and a bore which extends therebetween and which accommodates the cannula,
inserting the inner member into the bore of the outer member with one end of the inner member extending outwardly of the outer member thereby forming a cover for the cannula, and
joining the cannula hub to the cannula cover by engaging the one outwardly extending end of the inner member within the portion of the first member bore not occupied by the second member to thereby enclose the operative end of the cannula within the bore of the inner member.

9. A method according to claim 8 wherein said inner member insertion step includes inserting the inner member into the bore of the outer member with both ends of the inner member extending outwardly of the outer member to facilitate attachment of one of the ends to a fluid conduit.

10. A method according to claim 1, further comprising
wherein said second member insertion step includes inserting the second member into the bore of the first member with both opposite ends of the second member extending outwardly of the first member,
fabricating a third member having a generally uniform cross-sectional shape with an open interior and an open end to form a cover for the cannula, and
joining the cannula cover to the cannula hub with the open end of the cannula cover engaged in a fluid-tight relationship about the outwardly disposed end of the second member form which the cannula extends with the operative end of the cannula enclosed within the open interior of the cannula cover.

11. A method according to claim 3 and further comprising the step of
subsequent to said fabrication, insertion, securement and cannula cover joining steps, joining a fluid conduit to the first mentioned second member end.

12. A method of manufacturing a support assembly for a cannula having an operative end, said method comprising the steps of
fabricating a first member having a bore and a generally uniform cross-sectional shape,
fabricating a second member having a generally uniform cross-sectional shape with opposite ends and a bore extending therebetween which accommodates the cannula,
inserting the second member into the bore of the first member with both opposite ends of the second member extending outwardly of the first member, one end of the second member accomodating attachment to a fluid conduit, the assembled first and second members thereby forming a hub for the cannula,
securing the cannula within the bore of the second member so that the operative end of the cannula is supported in an outwardly exposed position beyond the end of the second member opposite to the first mentioned one second member end,
fabricating a third member having a generally uniform cross-sectional shape with an open interior and an open end to form a cover for the cannula,
joining the cannula cover to the cannula hub with the open end of the cannula cover engaged in a fluid-tight relationship about the outwardly disposed end of the second member from which the cannula extends with the operative end of the cannula enclosed within the open interior of the cannula cover,
fabricating a resiliently compressible fourth member,
press-fitting the fourth member into the open interior of the cannula cover to sealing enclose both the end of the cannula cover and the tip of the operative cannula end which is disposed therein when the cover is engaged on the hub, and
subsequent to said fabrication, insertion, securement and cover joining steps, joining a fluid conduit to the exposed one end of the second member opposite the cover.

* * * * *

UNITED STATES PATENT AND TRADEMARK OFFICE
CERTIFICATE OF CORRECTION

PATENT NO. : 4,574,456
DATED : March 11, 1986
INVENTOR(S) : Emil H. Soika

It is certified that error appears in the above-identified patent and that said Letters Patent are hereby corrected as shown below:

In the title, after "Manufacturing A" insert --Cannula--.

At column 4, line 59, change "drawrngs" to --drawings--.

At column 9, line 29, before "member", insert --third--.

At column 10, line 27, delete "15".

At column 11, line 36, change "oven" to --open--.

At column 11, line 65, change "embodiment" to --embodiments--.

In the claims:

In Claim 1, at column 12, line 51, after "assembly for" insert --a--; at column 12, line 53, before "steps" insert --the--; at column 12, line 54 after "bore and a" insert --generally--; at column 12, line 64, change "with" to --within--; at column 13, line 1, after "insertion and", insert --securement--.

In Claim 6, at column 13, line 37, after "tubular member upon the" insert --third--.

In Claim 12, at column 14, line 60, change "sealing" to --sealingly--.

Signed and Sealed this

Sixteenth Day of December, 1986

*Attest:*

DONALD J. QUIGG

*Attesting Officer*     *Commissioner of Patents and Trademarks*